United States Patent
Krebs et al.

(10) Patent No.: US 10,664,979 B2
(45) Date of Patent: May 26, 2020

(54) METHOD AND SYSTEM FOR DEEP MOTION MODEL LEARNING IN MEDICAL IMAGES

(71) Applicant: Siemens Healthcare GmbH, Erlangen (DE)

(72) Inventors: Julian Krebs, Moers (DE); Tommaso Mansi, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 132 days.

(21) Appl. No.: 16/131,465

(22) Filed: Sep. 14, 2018

(65) Prior Publication Data
US 2020/0090345 A1   Mar. 19, 2020

(51) Int. Cl.
*G06T 17/00* (2006.01)
*G06T 7/20* (2017.01)
*G06T 7/246* (2017.01)
*G06T 7/00* (2017.01)
*A61B 5/00* (2006.01)

(52) U.S. Cl.
CPC ............ *G06T 7/248* (2017.01); *A61B 5/4848* (2013.01); *A61B 5/7267* (2013.01); *G06T 7/0016* (2013.01); *G06T 2207/10016* (2013.01); *G06T 2207/20036* (2013.01); *G06T 2207/20081* (2013.01); *G06T 2207/20084* (2013.01); *G06T 2207/30004* (2013.01)

(58) Field of Classification Search
CPC ................. G06T 7/248; G06T 7/0016; G06T 2207/20036; G06T 2207/20084; G06T 2207/30004; G06T 2207/10016; A61B 5/4848; A61B 5/7267
See application file for complete search history.

(56) References Cited

U.S. PATENT DOCUMENTS

| | | | |
|---|---|---|---|
| 8,094,899 B2 | 1/2012 | Chouno | |
| 8,098,898 B2 | 1/2012 | Shimazu et al. | |
| 8,885,715 B2 | 11/2014 | Kurata | |
| 10,004,462 B2 | 6/2018 | Ernst et al. | |
| 10,043,269 B2 | 8/2018 | Wang et al. | |
| 2005/0096543 A1 | 5/2005 | Jackson et al. | |

(Continued)

OTHER PUBLICATIONS

Graves et al., "Neural Turing Machines," Dec. 10, 2014; Google DeepMind, London, UK, 26 pgs.

(Continued)

*Primary Examiner* — Syed Haider

(57) ABSTRACT

A method and system for computer-based motion estimation and modeling in a medical image sequence of a patient is disclosed. A medical image sequence of a patient is received. A plurality of frames of the medical image sequence are input to a trained deep neural network. Diffeomorphic deformation fields representing estimated motion between the frames of the medical image sequence input to the trained deep neural network are generated. Future motion, or motion between frames, is predicted from the medical image sequence and at least one predicted next frame is generated using the trained deep neural network. An encoding of the observed motion in the medical image sequence is also generated, which is used for motion classification (e.g., normal or abnormal) or motion synthesis to generate synthetic data.

22 Claims, 6 Drawing Sheets

(56) References Cited

U.S. PATENT DOCUMENTS

| | | | |
|---|---|---|---|
| 2007/0225574 A1* | 9/2007 | Ueda | A61B 5/00 600/300 |
| 2014/0093030 A1 | 4/2014 | Mukumoto et al. | |
| 2014/0128721 A1 | 5/2014 | Forthmann et al. | |
| 2015/0238148 A1* | 8/2015 | Georgescu | A61B 5/7267 600/408 |
| 2015/0297120 A1 | 10/2015 | Son et al. | |
| 2016/0073962 A1 | 3/2016 | Yu et al. | |
| 2016/0189394 A1 | 6/2016 | Zhang et al. | |
| 2016/0247293 A1 | 8/2016 | Beylin et al. | |
| 2016/0358334 A1 | 12/2016 | Osborne et al. | |
| 2017/0143271 A1 | 5/2017 | Gustafsson et al. | |
| 2019/0130565 A1* | 5/2019 | Lee | G06N 3/08 |
| 2019/0130639 A1* | 5/2019 | Boyce | G06F 3/013 |
| 2019/0384304 A1* | 12/2019 | Towal | G06K 9/00791 |

OTHER PUBLICATIONS

Gulcehre et al, "Memory Augmented Neural Networks with Wormhole Connections," Jan. 30, 2017, 27 pgs.

Rohe et al, "SVF-Net: Learning Deformable Image Registration Using Shape Matching", In Medical Image Computing and Computer Assisted Intervention, Jul. 6, 2017, 9 pgs.

Kingma et al., "Auto-Encloding Variational Bayes", Dec. 20, 2013, MICCAI, pp. 1-14.

Yang et al., "Prediction Based Collaborative Trackers (PCT): A Robust and Accurate Approach Toward 3D Medical Object Tracking," IEEE Transactions on Medical Imaging, vol. 30, No. 11, Nov. 2011, pp. 1921-1932.

De Craene et al., "Temporal Diffeomorphic Free-Form Deformation: Application to Motion and Strain Estimation from 3D Echocardiography," Medical Image Analysis, Oct. 26, 2011, 37 pgs.

* cited by examiner

METHOD AND SYSTEM FOR DEEP MOTION MODEL LEARNING IN MEDICAL IMAGES

BACKGROUND OF THE INVENTION

The present invention relates to estimating and modeling motion of structures or organs in a sequence of medical images, and more particularly to deep learning based modeling and prediction of motion in medical images.

Analyzing and modeling the motion of structures or organs in a sequence of medical images (e.g., cardiac medical images, abdominal medical images, etc.) is an important task in numerous clinical applications, such as image reconstruction, digital subtraction, and organ motion quantification. Having a unique representation of an organ motion can also enable identification of diseases visible through abnormal motion, such as cardiac arrhythmias. Due to these multiple applications, computer-based motion modeling has been the focus of intense research. A major difficult in motion modeling lies in the estimation of organ deformation, as well as the subsequent estimation of a representative motion model. Existing methods typically rely on hand-crafted algorithms which embed strong priors and are therefore not robust and not generalizable to changes of image quality, modality, organs, etc.

Typically, organ motion is studied by finding correspondences between the different frames in an image sequence. Dense correspondences are typically found with deformable registration in which objective functions including a similarity metric between deformed and final images are optimized. Due to the ill-posed nature of the problem, various regularizers are incorporated to add prior knowledge about the transformations under consideration. In order to compute trajectories in a series of frames, diffeomorphic, spatiotemporal B-spline parameterized velocity fields have been introduced. Due to 3D/4D B-spline grids, temporal consistency is taken into account by design. The similarity metric is computed as the sum of the differences between a chose template image and all consecutive frames. On approach proposed the use of barycentric subspaces as a projection space in which motion analysis can be done. Other approaches rely on optical flow to get the dense deformation through the time series, and then manifold learning across a population to learn a mean motion model.

Existing methods for motion modeling in medical imaging rely on time consuming optimization procedures, hand-picked regularizers, and manifold learning on engineered motion features. In cases in which a parameterized motion model is used, the parameterized motion model is constructed manually and typically lacks generalizability. The present inventors have recognized the need for a computer-based medical image motion modeling method that is generalizable to various medical imaging motion modeling tasks and robust to changes in image modality, quality, organs, etc.

BRIEF SUMMARY OF THE INVENTION

The present invention provides a method and system for computer-based motion estimation and modeling in medical images. Embodiments of the present invention provide systems and methods that learn a motion model by looking only at examples of image sequences. Embodiments of the present invention train a deep neural network that learns to extract features that describe motion of an organ and learns the manifold of possible trajectories to estimate the observed organ motion in an image sequence and predict the future deformations of the organ and/or deformations that occurred in between two observations.

In an embodiment of the present invention, a method for computer-based motion estimation and modeling in a medical image sequence of a patient comprises: receiving a medical image sequence of a patient; inputting a plurality of frames of the medical image sequence to a trained deep neural network; generating, using the trained deep neural network, diffeomorphic deformation fields representing estimated motion between the frames of the medical image sequence input to the trained deep neural network; generating an encoding of observed motion in the medical image sequence using the trained deep neural network; and predicting non-observed motion from the medical image sequence and generating at least one predicted frame using the trained deep neural network, wherein the at least predicted frame is one of a predicted future frame or a predicted frame between the frames of the medical image sequence input to the trained deep neural network.

In an embodiment, generating, using the trained deep neural network, diffeomorphic deformation fields representing estimated motion between the frames the medical image sequence input to the trained deep neural network comprises: generating, by the trained deep neural network for each frame input to the trained deep neural network, a dense velocity field that provides estimated velocities at each pixel in that frame; and generating a respective diffeomorphic deformation field for each frame input to the trained deep neural network by performing exponentiation of the dense velocity field generated for that frame, wherein the diffeomorphic deformation field provides estimated displacements between that frame and the next frame at each pixel.

In an embodiment, the method further comprises: generating a predicted frame for each frame input to the trained deep neural network by warping that frame based on the diffeomorphic deformation field estimated for that frame.

In an embodiment, predicting non-observed motion from the medical image sequence and generating at least one predicted frame using the trained deep neural network comprises: generating a predicted frame between the frames of the medical image sequence by: inputting a frame of the medical image sequence to the trained deep neural network; generating, by the trained deep neural network, a predicted dense velocity field that provides estimated velocities at each pixel in the input frame of the medical image sequence; generating a predicted diffeomorphic deformation field that provides predicted displacements between the input frame and a time point between the input frame and a next frame in the medical image sequence at each pixel by performing exponentiation of the predicted dense velocity field; and generating a predicted frame between the input frame and the next frame of the medical image sequence by warping the input frame based on the predicted diffeomorphic deformation field.

In an embodiment, predicting non-observed motion from the medical image sequence and generating at least one predicted frame using the trained deep neural network comprises: generating a predicted future frame by: inputting a final frame of the medical image sequence to the trained deep neural network; generating, by the trained deep neural network, a predicted dense velocity field that provides estimated velocities at each pixel in the final frame of the medical image sequence; generating a predicted diffeomorphic deformation field by performing exponentiation of the predicted dense velocity field; and generating a predicted next frame subsequent to the final frame of the medical image sequence by warping the final frame of the medical image sequence based on the predicted diffeomorphic deformation field.

In an embodiment, predicting non-observed motion from the medical image sequence and generating at least one predicted frame using the trained deep neural network further comprises: generating a predicted future frame by: (a) inputting the predicted next frame to the trained deep neural network, (b) generating, by the trained deep neural network, a predicted dense velocity field for the input predicted next frame, (c) generating a predicted diffeomorphic deformation field for the input predicted next frame by performing exponentiation of the predicted dense velocity field for the input predicted next frame, (d) generating a subsequent predicted next frame by warping the input predicted next frame based on the predicted diffeomorphic deformation field generated for the input predicted next frame, and (e) repeating steps (a)-(d) for each of plurality of predicted next frames.

In an embodiment, the trained deep neural network comprises: a convolutional encoder-decoder that inputs each frame and includes an output layer that generates a dense velocity field for each frame that provides estimated velocities at each pixel in that frame; an exponentiation layer that performs exponentiation of the dense velocity field generated for each frame to generate the diffeomorphic deformation field for each frame; and a warping layer that warps each frame based on the diffeomorphic deformation field generated for each frame to generate a predicted next frame for each frame.

In an embodiment, the trained deep neural network is trained based on a plurality of training medical image sequences to minimize a loss function that compares a final frame of each training medical image sequence with a predicted final frame generated from each previous frame in the training medical image sequence by warping each previous frame based on a sum of the dense velocity field generated for that frame and the dense velocity fields generated for all intermediate frames between that frame and the final frame.

In an embodiment, an encoder part of the convolutional encoder-decoder comprises a variational autoencoder that forces the estimated deformation field into a latent space distribution that is learned from the training medical image sequences.

In an embodiment, the deep neural network further comprises a memory module that is trained to learn a temporal motion model from the training medical image sequences, and the memory module is implemented using a recurrent neural network or a memory network.

In an embodiment, wherein generating an encoding of observed motion in the medical image sequence using the trained deep neural network comprises: outputting encoded motion parameters generated by an encoder part of the convolutional encoder-decoder for the frames of the medical image input to the trained deep neural network.

In an embodiment, the method further comprises: classifying the medical image sequence based on the encoded motion parameters to detect disease, classify the patient, or predict outcome of a treatment.

In an embodiment, the method further comprises: performing motion synthesis from an input medical image that is not in the sequence of medical images using the encoded motion parameters to generate a synthetic sequence of medical images.

In an embodiment of the present invention, an apparatus for motion estimation and modeling in a medical image sequence of a patient comprises: means for receiving a medical image sequence of a patient; means for inputting a plurality of frames of the medical image sequence to a trained deep neural network; means for generating, using the trained deep neural network, diffeomorphic deformation fields representing estimated motion between the frames of the medical image sequence input to the trained deep neural network; means for generating an encoding of observed motion in the medical image sequence using the trained deep neural network; and means for predicting non-observed motion from the medical image sequence and generating at least one predicted frame using the trained deep neural network, wherein the at least predicted frame is one of a predicted future frame or a predicted frame between the frames of the medical image sequence input to the trained deep neural network.

In an embodiment of the present invention, a non-transitory computer readable medium storing computer program instructions for computer-based motion estimation and modeling in a medical image sequence of a patient. The computer program instructions when executed by a processor cause the processor to perform operations comprising: receiving a medical image sequence of a patient; inputting a plurality of frames of the medical image sequence to a trained deep neural network; generating, using the trained deep neural network, diffeomorphic deformation fields representing estimated motion between the frames of the medical image sequence input to the trained deep neural network; generating an encoding of observed motion in the medical image sequence using the trained deep neural network; and predicting non-observed motion from the medical image sequence and generating at least one predicted frame using the trained deep neural network, wherein the at least predicted frame is one of a predicted future frame or a predicted frame between the frames of the medical image sequence input to the trained deep neural network.

These and other advantages of the invention will be apparent to those of ordinary skill in the art by reference to the following detailed description and the accompanying drawings.

DETAILED DESCRIPTION

The present invention relates to computer-based motion estimation and modeling in medical images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or a remote computer system.

Embodiments of the present invention provide systems and methods that learn a motion model by looking only at examples of image sequences. Embodiments of the present invention train a deep neural network (DNN) that learns to extract features that describe motion of an organ and learns the manifold of possible trajectories to estimate the observed organ motion in an image sequence and predict the future deformations of the organ and/or deformations that occurred in between two observations. The results output by the trained DNN include dense trajectories between the frames of a medical image sequence and a projection of the motion to a low-dimensional parameterized space. These motion estimation and modeling results can be utilized in various advantageous applications. For example, the dense trajectories/deformations estimated using the DNN can be used to predict future motion, compensate for motion (e.g., cardiac or respiratory motion), and to interpolate between the time frames of the medical image sequence to achieve a higher temporal resolution. The motion parameters encoded in a low-dimensional parameterized space can be used to assess or classify abnormal organ motion as diseases associated with such abnormal organ motion and to provide a generative model to simulate motion for medical images. For example, such a generative model can be used to apply a typically diseased motion pattern on given images. Furthermore, as embodiments of the present invention provide a generative motion model, the trained DNN can also be used to generate realistic organ motions which can be used for further artificial intelligence (AI) training.

Embodiments of the present invention utilizes a deep neural network architecture for motion learning, which not only capture dense motion from sequences of medical images over time, but also learns an interpretable and generative motion model purely from training data. The deep neural network framework described herein can be applied in both unsupervised and supervised learning approaches.

Figure 1:
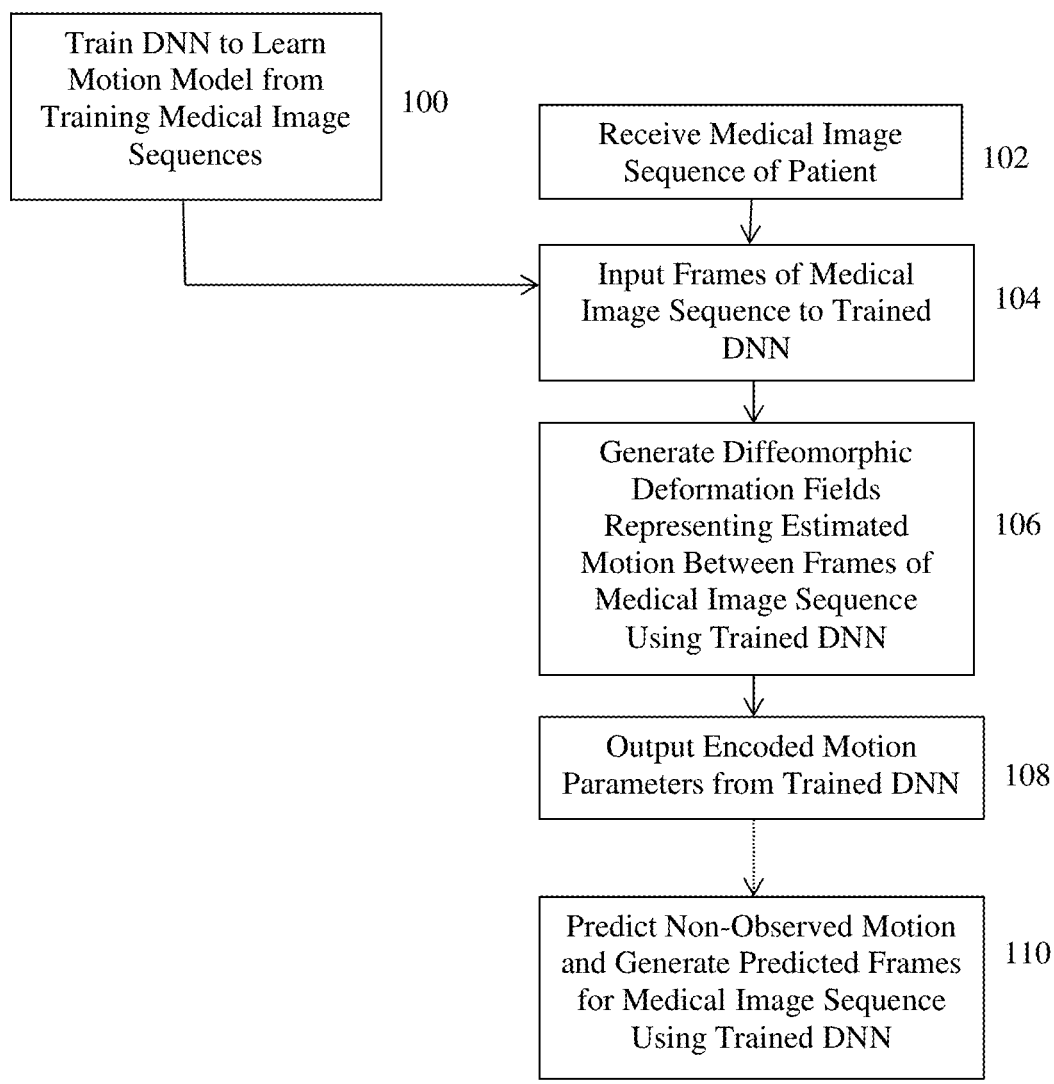
FIG. 1 illustrates a method for computer-based motion estimation and modeling in medical images according to an embodiment of the present invention.

FIG. 1 illustrates a method for computer-based motion estimation and modeling in medical images according to an embodiment of the present invention. Referring to FIG. 1, at step 100, a deep neural network (DNN) is trained to learn a motion model from training medical image sequences. Step 100 is performed in an offline training stage to train the DNN prior to the on-line motion estimation and modeling for newly input/received medical image sequences performed in steps 102-110.

The DNN can be trained to learn a motion model from a large database of medical image sequences. The training medical image sequences used to train the DNN can be time sequences of medical images acquired using any imaging modality. For example, the training medical image sequences may be sequences of magnetic resonance (MR) images, computed tomography (CT) images, ultrasound images, x-ray images, or medical images acquired using any other medical imaging modality. The training medical image sequences can be sequences of 2D medical images or 3D medical images (volumes). The individual medical images in a given medical image sequence are referred to as "frames." According to an advantageous implementation, the training medical image sequences used to train the DNN can include multiple medical image sequences of the same organ (e.g., heart, lungs, etc.) or region of the body (e.g., cardiac images, abdominal images, etc.) in order to train the DNN to learn a manifold of possible trajectories for the motion of that organ or region of the body. The training medical image sequences can be medical image sequences acquired from various patients that are stored in a databased in a storage or memory of a computer system and retrieved from the database to perform the training of the DNN. For example, the training medical image sequences can be retrieved from a locally stored database or a database stored on a remote server or cloud-based storage.

The training medical images are used to train a recursive and generative DNN. For example, the DNN can be recursively applied to each frame in a given medical image sequence to generate for each frame an estimated deformation field representing the motion between that frame and a next frame in the sequence, as well as a predicted next frame that is a warped image resulting from warping the current frame using the estimated deformation field. In an advantageous embodiment, the DNN can be implemented using an image-to-image architecture that, given two images (i.e., two frames of a medical image sequence) as input, estimates a diffeomorphic deformation field. Alternatively, the DNN can sequentially input one frame at time or can input N frames at a time.

Figure 2:
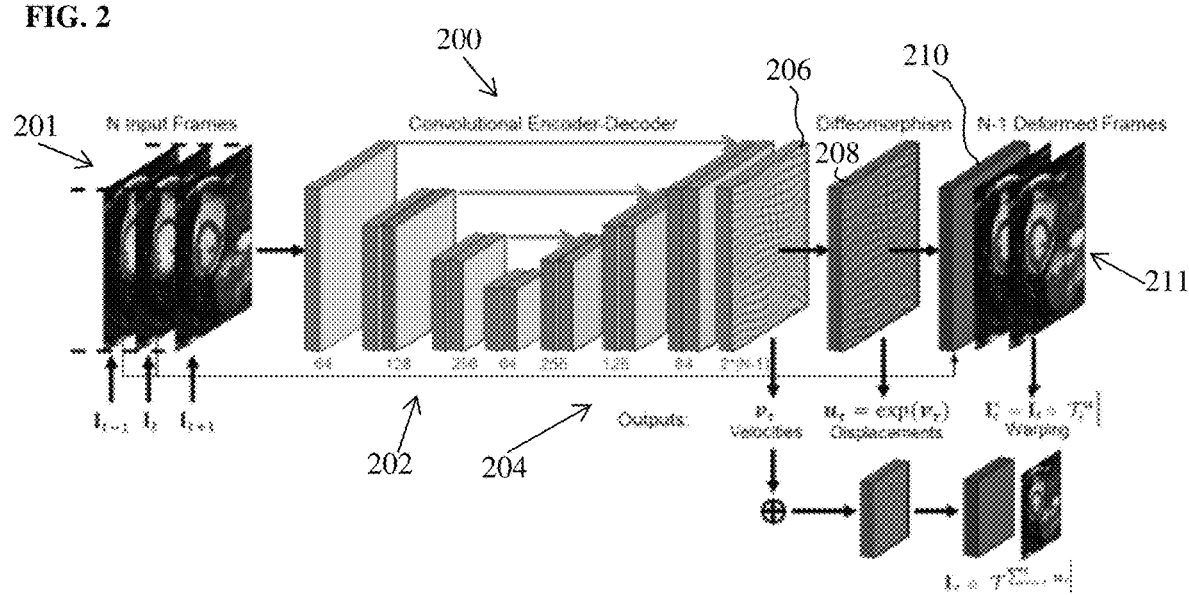
FIG. 2 illustrates an image-to-image architecture for a deep neural network (DNN) according to an embodiment of the present invention.

FIG. 2 illustrates an image-to-image architecture for the DNN according to an embodiment of the present invention. As shown in FIG. 2, the image-to-image architecture for the DNN can be implemented using a convolutional encoder-decoder 200. The convolutional encoder-decoder 200 inputs frames 201 of a medical image sequence. The convolutional encoder-decoder 200 includes an encoder part 202 that has a series of layers that encode each input image into a code whose size is substantially less than the size of the input image and a decoder part 204 that has a series of layers that will then decode the code representing each input image into a respective output image. The encoder part 202 of the convolutional encoder-decoder 200 alternates convolutional layers and max-pooling layers and the decoder part 204 of the convolutional encoder-decoder 200 alternates convolutional layers and up-sampling layers. The number immediately below each convolutional layer in the convolutional encoder-decoder 200 of FIG. 2 indicates a number of output channels for the convolutional layer (i.e., a number of feature maps generated by the convolutional layer). An element-wise activation function is also applied to the feature maps after each convolutional layer. In an exemplary embodiment, rectified linear (ReLU) can be used for the activation function for each convolutional layer, but the present invention is not limited thereto. An output layer 206 generates a velocity field for each input frame from the feature maps output from the final layer of the decoder part 204. The velocity field estimated for each input frame is a dense velocity field that provides estimated velocities of the organ/structures at each pixel (or voxel) of the input frame. An exponentiation layer 208 performs exponentiation of the velocity field to generate a dense diffeomorphic deformation field for each frame that represents the organ/structure motion between that frame and a next frame in the medical image sequence. The dense diffeomorphic field provides estimated displacements of the organ/structure at each pixel (or voxel) of the input frame. A warping layer 210 warps each input frame based on the diffeomorphic deformation field generated for that frame in order to generate a deformed frame 211 that provides a prediction for the next frame in the medical image sequence. In the architecture of FIG. 2, the exponentiation and warping layers 208 and 210 are differentiable implementations of the respective operations. The velocity field exponentiation can be performed using either geodesic shooting or through scaling and squaring. Both the exponentiation and the warping rely on vector field composition, which can be implemented in a differentiable way an integrated directly into the neural network as a specific layer.

N frames 201 of a medical image sequence are input to the convolutional encoder-decoder 200, where the current frame being processed is referred to as $I_t$. The frames 201 can be sequentially input one at a time, or two or more frames can be input together. For each current frame $I_t$, the output layer 206 of the convolutional encoder-decoder 200 generates a velocity field $v_t$, the exponentiation layer 208 generates a diffeomorphic deformation $u_t$ which represents the pixel-by-pixel displacements between the current frame $I_t$ and the next frame $I_{t+1}$ in the sequence, and the warping layer 210 generates a deformed frame $I^*_t = I_t \circ \mathcal{T}_t^u$ by warping the current image $I_t$ based on the deformation generated by the exponentiation layer 208, where $\mathcal{T}_t^u$ is a transformation based on the deformation field u. The outputs of the trained DNN include the set of velocity fields $v_\tau$ estimate for all of the N frames of the medical image sequence, the diffeomorphic deformation fields (displacements) $u_\tau$ estimated for all of the N frames of the medical image sequence and the deformed frame $I^*_t = I_t \circ \mathcal{T}_t^u$ estimated from each frame of the medical image sequence.

Figure 3:
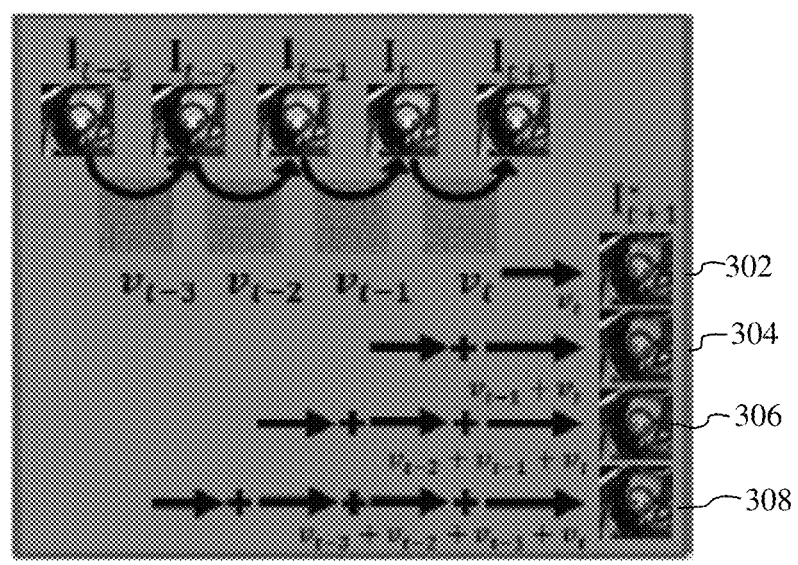
FIG. 3 illustrates generating a predicted last frame from each previous frame of a medical image sequence in order to train the DNN based on a loss function that enforces temporal consistency according to an embodiment of the present invention.

According to an advantageous embodiment, a temporal consistency loss is used to incorporate temporal knowledge in the estimation of the deformation field between each pair of frames for robust motion learning. In addition to directly estimation the velocities and deformations between frames of a given medical image sequence by the convolutional encoder-decoder, a set of previous frames in the image sequence is used to estimate the dense deformation from one frame to the other. Basically, for a given medical image sequence, each previous frame is registered to the last frame by adding up the velocities of the intermediate frames. That is, a predicted last frame is generated from each previous frame in the image sequence by warping each previous frame based on the sum of the pixel-wise velocities estimated for all of the intermediate frames by the convolutional encoder-decoder. FIG. 3 illustrates generating a predicted last frame from each previous frame of a medical image sequence in order to train the DNN based on a loss function that enforces temporal consistency according to an embodiment of the present invention. As shown in FIG. 3, a medical image sequence includes frames $I_{t-3}, I_{t-2}, I_{t-1}, I_t$, and $I_{t+1}$. A predicted last frame $I^*_{t+1}$ is generated from each previous frame $I_{t-3}, I_{t-2}, I_{t-1}$, and $I_t$ based on the sum of velocities computed for that frame and the intermediate frames. In particular, predicted last frame 302 is generated is generated by deforming frame $I_t$ based on the velocity field $v_t$. Predicted frame 304 is generated by deforming frame $I_{t-1}$ based on the sum of the velocity fields $v_{t-1}+v_t$. Predicted frame 306 is generated by deforming frame $I_{t-2}$ based on the sum of the velocity fields $v_{t-2}+v_{t-1}+v_t$. Predicted frame 308 is generated by deforming frame $I_{t-3}$ based on the sum of the velocity fields $v_{t-3}+v_{t-2}+v_{t-1}+v_t$. Layers 212, 214, and 216 shown in FIG. 2 are used to perform these operations during training to implement training using temporal consistency loss. Layer 212 adds the velocity field $v_t$ estimated for the current frame $I_t$ to the set of velocity fields $v_\tau$ previously estimated for the previous layers. Layer 214 generates a diffeomorphic deformation for each previous frame based on the sum of the velocity fields of estimate for that frame and each subsequent frame. Layer 216 warps each previous frame based on the diffeomorphic deformation generated for each previous frame to generate a respective warped frame 217 that is a prediction for the last frame in the sequence. The warped images (last frame predictions) generated from all of the frames in the sequence are all output from the network and the loss is computed with respect to a similarity metric comparing all warped frames with the actual last frame of the sequence. Backpropagation is used to learn network parameters (weights) that minimize the loss function over the set of training medical image sequences. The use of predictions generated from multiple frames in each sequence helps to robustly handle noisy data and leads to a more robust motion estimation.

According to an advantageous embodiment, a variational autoencoder (VAE) can be used to force the estimated deformation fields to lay in a latent space z that is learned directly from the data. Gaussian VAE, mixture of Gaussion, or Bayesian/Generative Adversarial Network (GAN) VAE can be used as well, for richer motion model representation. In one embodiment, Enc(x) (i.e., the output of the encoder of the convolutional encoder-decoder) can be forced to be similar to a predefined prior distribution p(z) by adding the Kullback-Leibler divergence as part of the loss function during training. The prior is considered to be the unit normal distribution N(0,I):

KL(Enc(x)∥N(0,I)).

Figure 4:
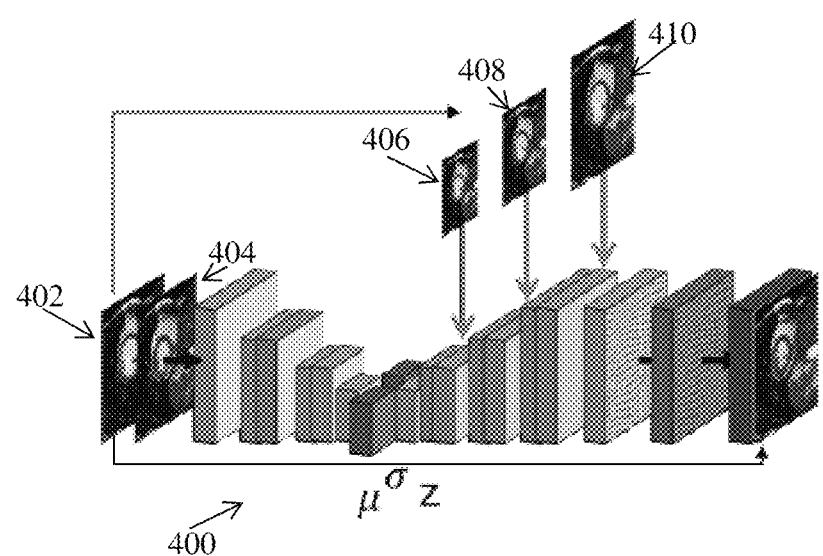
FIG. 4 illustrates conditioning a variational autoencoder by infusing downsampled versions of the moving image to the decoder according to an embodiment of the present invention.

The second part of the autoencoder loss, the reconstruction loss function, can be replaced with any similarity metric (and regularizer) as used in pair-wise registration. In addition, in an advantageous implementation, the variational autoencoder can be conditioned by infusing downsampled versions of the moving image ($I_t$) to the decoder part of the network. FIG. 4 illustrates conditioning the variational autoencoder by infusing downsampled versions of the moving image to the decoder according to an embodiment of the present invention. As shown in FIG. 4, two consecutive frames 402 and 404 are input to the convolutional encoder-decoder 400. The first frame 402 is considered to be the moving image, and the network 400 estimates the velocity field between the first frame 402 and the second frame 400. The architecture of the convolutional encoder-decoder network 400 can be implemented as described above in connection with FIG. 2. Downsampled versions 406, 408, and 410 of frame 402 are generated and input to the convolutional layers of the decoder part of the network. The autoencoder loss (e.g., including the Kullback-Leibler divergence and the similarity metric) is calculated between the output of each convolutional layer of the decoder part and the respective downsampled version 406, 408, and 410 of frame 402. This conditioning results in generating a more accurate deformation field than a deformation field estimated from the latent code alone. Instead, this conditioning forces the deformation field to "fit" the image that is going to be warped. The latent code $\mu^o z$ generated by the autoencoder provides a projection of the motion to a low-dimensional parameterized space. Since the latent space distribution (latent code) is interpretable, this space can be used for motion analysis and also for generating motion given a moving image. Another advantage of the variational autoencoder is the implicit regularization of the DNN's output in general.

According to an advantageous embodiment, a memory module can be used to "summarize" the motion in a medical image sequence over time for motion analysis tasks. The memory module is trained to learn a temporal motion model from the training medical image sequences. For example, the memory module can be trained to learn motion for a whole cardiac sequence. In an implementation in which the frames are sequentially input one at a time, the memory state of the memory module can be used together with the features generated by the convolutional encode-decoder for each frame to predict the velocity field for each frame. The memory module may also be used to apply the learned motion model to predict future motion for a given image. The memory module can be implemented using a recurrent neural network (RNN) or a memory network. For example, in a possible implementation, the latent space layer of z can be realized using a convolutional long short-term memory (LSTM) layer. Other methods for memory incorporation, such as external memory or Neural Turing machines, are possible as well. The DNN can learn and store different motion models. Using Neural Turing Machine architectures, with context-specific reading heads, the appropriate motion model is selected as used.

Returning to FIG. 1, once the DNN is trained to learn the motion model in the training stage 100, the trained DNN is stored, for example on a storage or memory of a computer system, and can then be used to perform on-line motion estimation and modeling for newly input/received medical image sequences performed in steps 102-110.

At step 102, a medical image sequence of a patient is received. The medical image sequence can be a time sequence of medical images acquired using any medical imaging modality. For example, the medical image sequence may be a sequence of magnetic resonance (MR) images, computed tomography (CT) images, ultrasound images, x-ray images, or medical images acquired using any other medical imaging modality. The medical image sequence can be sequences of 2D medical images or 3D medical images (volumes). The medical image sequence can be a sequence of medical images of a particular organ (e.g., heart, lungs, etc.) or region of the body (e.g., cardiac images, abdominal images, etc.). The medical image sequence can be received directly from an image acquisition device, such as an MR scanner, CT scanner, etc., as the medical image sequence of the patient is acquired, or can be received by loading a previously acquired medical image sequence of the patient.

At step 104, the frames of the medical image sequence are input to the trained DNN. In a possible implementation, the trained DNN recursively inputs the medical image sequence frame-by-frame. Alternatively, the trained DNN can input N frames together. In an exemplary implementation, starting with the first frame in the sequence, the trained DNN inputs a current frame ($I_t$) and a next frame ($I_{t+1}$). The current frame $I_t$ is considered a moving image and the next frame $I_{t+1}$ is considered a reference image. The trained DNN estimates a dense velocity field $v_t$ that provides estimated velocities of the organ/structures at each pixel (or voxel) in the current frame and a diffeomorphic deformation field $u_t$ that represents the pixel-wise motion between the current frame $I_t$ and the next frame $I_{t+1}$. The trained DNN then inputs the next pair of frames with the previous "next frame" $I_{t+1}$ now input as the current frame $I_t$. This is repeated until the final frame of the medical image sequence is reached. In a possible embodiment, the frames of the medical image sequence can be input to the trained DNN in real time or near real time as they are received from the medical image acquisition device. Alternatively, all or part of the medical image sequence can be acquired prior to sequentially inputting the frames to the trained DNN.

At step 106, diffeomorphic deformation fields representing estimated motion between the frames of the medical image sequence are generated using the trained DNN. The trained DNN can have a convolutional encoder-decoder architecture as described above and shown in FIG. 2. For each current frame $I_t$ input to the trained DNN, the convolutional encoder-decoder processes the current frame $I_t$ and generate a dense velocity field $v_t$ that provides a pixel-wise map of estimated velocities for the current frame. In an exemplary implementation, the convolutional encoder-decoder can processes the current frame $I_t$ and the next frame $I_{t+1}$ together in order to generate the estimated velocity field $v_t$. In another exemplary implementation, the convolutional encoder-decoder may process each current frame $I_t$ one at a time and generate each velocity field $v_t$ using the features extracted from the current frame $I_t$ and the memory state of the memory module (e.g., convolutional LSTM). An exponentiation layer performs exponentiation of the velocity field $v_t$ to generate a dense diffeomorphic deformation field $u_t$ for the current frame $I_t$ that represents the organ/structure motion between the current frame $I_t$ and the next frame $I_{t+1}$ in the medical image sequence. The diffeomorphic deformation field $u_t$ is a map of pixel-wise displacements of the organ/structure from the current frame $I_t$ and the next frame $I_{t+1}$. The dense diffeomorphic deformation field $u_t$ generated for each current frame $I_t$ can be output, for example by displaying each generated dense diffeomorphic deformation field $u_t$ on a display device of a computer system. This can result is a sequence of dense deformation fields representing the estimated motion of the organs/structures in the medical image sequence being displayed. In addition, each generated dense diffeomorphic deformation field $u_t$ (representing estimated motion between two frames of the medical image sequence) is stored in a storage and/or memory of a computer system. The estimated dense velocity field $v_t$ generated each current frame $I_t$ can also be output, for example by displaying each estimated dense velocity field $v_t$ on the display device. This can result is a sequence of dense velocity fields being displayed. In addition, each estimated dense velocity deformation field $v_t$ is stored in a storage and/or memory of a computer system.

At step 108, encoded motion parameters are output from the trained DNN. The trained DNN generates an encoding of the observed motion in the medical image sequence. In particular, the encoder part of the convolutional encoder-decoder used to implement the trained DNN generates low dimensional feature maps that encode the motion in each frame of the medical image sequence in a low dimensional parameterized space. These feature maps generated by the encoder part of the convolutional encoder-decoder provide encoded motion parameters ($\mu°z$ in FIG. 3) that characterize the relevant motion information in each frame of the medical image sequence. These encoded motion parameters (feature maps) can be output by storing the encoded motion parameters generated by the encoder part of the convolutional encoder-decoder in storage or memory of a computer system The encoded motion parameters may also be displayed, for example on a display device of a computer system.

The output encoded motion parameters are interpretable and can be used for motion analysis and classification. For, example the encoded motion parameters can be used to assess or classify abnormal motion, to detect disease, to classify the patient, and/or to predict outcome of a treatment. In a possible implementation, the encoded motion parameters can be input to a machine learning model trained to perform such classification based on the encoded motion parameters. The output encoded motion parameters can also be used in a generative model to perform motion synthesis to simulate motion similar to the observed motion in the received medical image sequence given a medical image. In this case, the observed motion parameters can be applied to an input medical image to generate a synthetic sequence of medical images from the input medical image. For example, encoded motion parameters estimated by the encoder part of the convolutional encoder-decoder from a medical image sequence from a patient with a particular disease (e.g., coronary disease) can be used to simulate a diseased motion pattern on other input medical images. Further, the encoded motion parameters generated from the received medical image sequence can also be used to simulate motion beyond the final frame of the received medical image sequence.

At step 110, non-observed motion is predicted and predicted frames are generated for the medical image sequence using the trained DNN. As used herein, non-observed motion refers to future motion (subsequent to the received medical image sequence) or motion in-between frames of the medical image sequence. The trained DNN can generate predicted frames in between frames of the medical image sequence, as well as predicted future frames subsequent to the medical image sequence.

In order to generate predicted frames in between frames of the medical image sequence, the trained DNN estimates the velocity field for a particular input frame and then generates a predicted diffeomorphic deformation field that provides predicted displacements between the input frame and a time point between the input frame and the next frame in the medical image sequence by performing exponentiation of the velocity field. The warping layer than warps the input frame based on the predicted diffeomorphic deformation field to generate a predicted frame between the input frame and the next frame of the medical image sequence.

In order to predict future motion of the patient's organs/structures from the medical image sequence, the trained DNN inputs the final frame of the medical image sequence and the current frame, and estimates a predicted velocity field and predicted deformation field for the final frame. The predicted velocity field for the final frame is estimated based on features extracted from the final frame by the convolutional encoder-decoder and a learned memory module that applies encoded motion parameters estimated from previous frames to predict the pixel-wise velocities in final frame. The exponentiation layer performs exponentiation of the predicted velocity field to generate the predicted deformation field. A warping layer warps the final frame on the medical image sequence based on the predicted deformation field generated for the final frame in order to generate a prediction next frame. This can be repeated to predict multiple future frames (i.e., predict motion of the patient's organs/structures over time) by inputting each predicted frame to the trained DNN as the current frame.

The predicted frames, including predicted future frames and predicted frames between existing frames of the medical image sequence, can be output, for example by displaying the predicted frames on a display device of a computer system. The predicted frames can also be stored in a storage or memory of a computer system. In addition to predicting non-observed motion (future frames and in-between frames), the warping layer may also warp each current frame $I_t$ in the medical image sequence to generate a respective predicted next frame $I^*_{t+1}$ that is a prediction for the next frame $I_{t+1}$ in the medical image sequence. These predicted next frames can also be output, for example by being displayed a display device of a computer system and stored in a storage or memory of a computer system.

Figure 5:
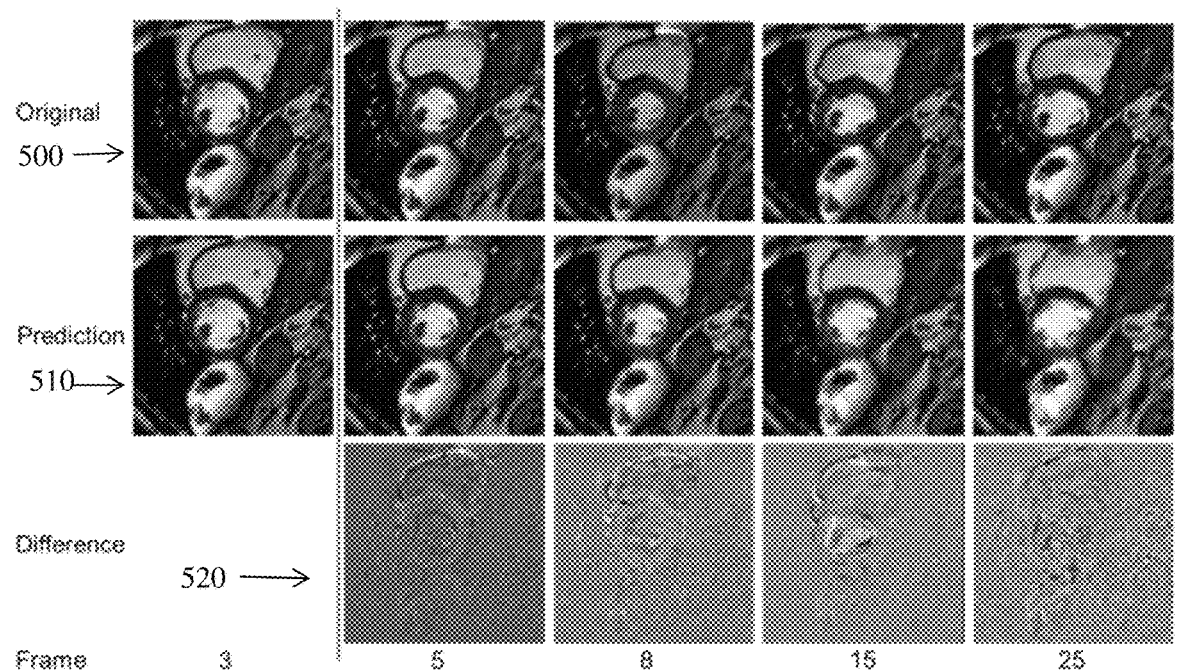
FIG. 5 illustrates exemplary results of motion prediction over time in cardiac medical image sequences using the method of FIG. 1.

FIG. 5 illustrates exemplary results of motion prediction over time in cardiac medical image sequences using the method of FIG. 1. In the example of FIG. 5, the DNN takes the first four frames of a cardiac medical image sequence as input and predicts the fifth frame. Additional predicted future frames are then predicted through auto regression by using the previously predicted frames as input for the next frame prediction. The bottle-neck layer used in this example is a convolutional LSTM. As shown in FIG. 5, row 500 shows the original images for frames 3, 5, 8, 15, and 25 of the cardiac medical image sequence and row 510 shows the predicted images for frames 3, 5, 8, 15, and 25. Row 520 shows the difference between the original and predicted images for frames 5, 8, 15, and 25.

Since the DNN described above is able to learn a generic motion model, it is possible to apply the motion model learned from one image domain to medical images from other medical imaging modalities. In addition, it is also possible that images of the same organ, but acquired using different medical imaging modalities, can be employed for training. For example, both ultrasound and MR cardiac images can be used together during training to learn the complete twisting deformation of the heart.

The embodiments of the present invention described above learn a generative motion model from examples of image sequences that fits the data and does not require hand-crafted features. The learned motion model can be used for motion analysis, sampling, and prediction. The generalizability of the above described method allows for learning motion models from different kinds of data (while only retraining on new data).

At testing time, the trained DNN takes tens of milliseconds for dense motion estimations, whereas variational state-of-the-art methods require minutes or hours. Compared to other unsupervised deep learning based registration algorithms, the dense outputs are guaranteed to be diffeomorphic and are implicitly regularized due to the use of a variational autoencoder. The use of temporal consistency loss and a memory module allow for capturing the temporal dependencies and model motion in longer sequences.

In possible embodiments of the present invention, neural networks with memory are used to encode various motion models implicitly, learned from data.

The embodiments of the present invention described above utilize a supervised approach for training the DNN. In other possible embodiment, deep reinforcement learning may be used to train the DNN. In this case, the network has the same architecture. However, the output is to predict motion, i.e., the action is a generated motion from the learned generative motion model. The reward is then calculated by comparing the prediction with the observation, and a policy to generate new motions by sampling is learned. Other deep reinforcement strategies could also apply.

Figure 6:
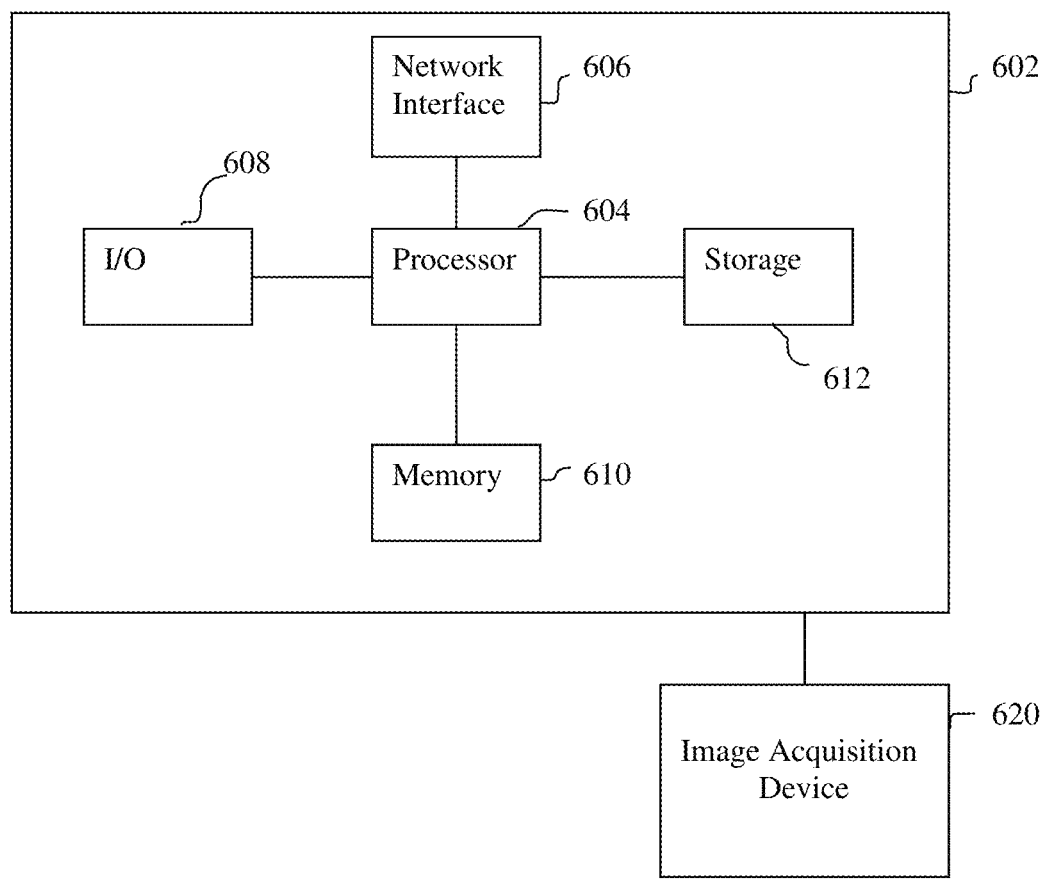
FIG. 6 is a high-level block diagram of a computer capable of implementing the present invention.

The above-described methods can be implemented on one or more computers using computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the method of FIG. 1 may be defined by the computer program instructions stored in the memory 610 and/or storage 612 and controlled by the processor 604 executing the computer program instructions. An image acquisition device 620, such as a CT scanning device, X-ray scanning device, C-arm image acquisition device, MR scanning device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). One skilled in the art will recognize that an implementation of an actual computer could contain other components as well, and that FIG. 6 is a high level representation of some of the components of such a computer for illustrative purposes.

In one embodiment, the computer that performs one or more of the above described methods may be integrated into a medical image scanner (image acquisition device). In another embodiment, the computer that performs one or more of the above described methods may be a mobile device, such as a smart phone or tablet. In another embodiment, the computer that performs one or more of the above described methods may be part of a patient monitoring system.

In another embodiment, one or more of the above described methods may be implemented in network-based cloud computing system. In such a network-based cloud computing system, a server communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. Certain steps of the above described methods may be performed by a server or by other computers/processors in the network-based cloud-computing system. Certain steps of the above described methods may be performed locally by a client computer in a network-based cloud computing system. The steps of the above described methods may be performed by one or more devices in the network-based cloud-computing system or by a local client computer in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for computer-based motion estimation and modeling in a medical image sequence of a patient, comprising:
   receiving a medical image sequence of a patient;
   inputting a plurality of frames of the medical image sequence to a trained deep neural network;
   generating, using the trained deep neural network, diffeomorphic deformation fields representing estimated motion between the frames of the medical image sequence input to the trained deep neural network, wherein generating, using the trained deep neural network, diffeomorphic deformation fields representing estimated motion between the frames of the medical image sequence input to the trained deep neural network comprises:
      generating, by the trained deep neural network for each frame input to the trained deep neural network, a dense velocity field that provides estimated velocities at each pixel in that frame; and
      generating a respective diffeomorphic deformation field for each frame input to the trained deep neural network by performing exponentiation of the dense velocity field generated for that frame, wherein the diffeomorphic deformation field provides estimated displacements between that frame and the next frame at each pixel;
   generating an encoding of observed motion in the medical image sequence using the trained deep neural network; and
   predicting non-observed motion from the medical image sequence and generating at least one predicted frame using the trained deep neural network, wherein the at least one predicted frame is one of a predicted future frame or a predicted frame between the frames of the medical image sequence input to the trained deep neural network.

2. The method of claim 1, further comprising:
   generating a predicted frame for each frame input to the trained deep neural network by warping that frame based on the diffeomorphic deformation field estimated for that frame.

3. The method of claim 1, wherein predicting non-observed motion from the medical image sequence and generating at least one predicted frame using the trained deep neural network comprises:
   generating a predicted frame between the frames of the medical image sequence by:
      inputting a frame of the medical image sequence to the trained deep neural network;
      generating, by the trained deep neural network, a predicted dense velocity field that provides estimated velocities at each pixel in the input frame of the medical image sequence;
      generating a predicted diffeomorphic deformation field that provides predicted displacements between the input frame and a time point between the input frame and a next frame in the medical image sequence at each pixel by performing exponentiation of the predicted dense velocity field; and
      generating a predicted frame between the input frame and the next frame of the medical image sequence by warping the input frame based on the predicted diffeomorphic deformation field.

4. The method of claim 1, wherein predicting non-observed motion from the medical image sequence and generating at least one predicted frame using the trained deep neural network comprises:

generating a predicted future frame by:
inputting a final frame of the medical image sequence to the trained deep neural network;
generating, by the trained deep neural network, a predicted dense velocity field that provides estimated velocities at each pixel in the final frame of the medical image sequence;
generating a predicted diffeomorphic deformation field by performing exponentiation of the predicted dense velocity field; and
generating a predicted next frame subsequent to the final frame of the medical image sequence by warping the final frame of the medical image sequence based on the predicted diffeomorphic deformation field.

5. The method of claim 4, wherein predicting non-observed motion from the medical image sequence and generating at least one predicted frame using the trained deep neural network further comprises:
generating a predicted future frame by:
(a) inputting the predicted next frame to the trained deep neural network,
(b) generating, by the trained deep neural network, a predicted dense velocity field for the input predicted next frame,
(c) generating a predicted diffeomorphic deformation field for the input predicted next frame by performing exponentiation of the predicted dense velocity field for the input predicted next frame,
(d) generating a subsequent predicted next frame by warping the input predicted next frame based on the predicted diffeomorphic deformation field generated for the input predicted next frame, and
(e) repeating steps (a)-(d) for each of plurality of predicted next frames.

6. The method of claim 1, wherein the trained deep neural network comprises:
a convolutional encoder-decoder that inputs each frame and includes an output layer that generates a dense velocity field for each frame that provides estimated velocities at each pixel in that frame;
an exponentiation layer that performs exponentiation of the dense velocity field generated for each frame to generate the diffeomorphic deformation field for each frame; and
a warping layer that warps each frame based on the diffeomorphic deformation field generated for each frame to generate a predicted next frame for each frame.

7. The method of claim 6, wherein the trained deep neural network is trained based on a plurality of training medical image sequences to minimize a loss function that compares a final frame of each training medical image sequence with a predicted final frame generated from each previous frame in the training medical image sequence by warping each previous frame based on a sum of the dense velocity field generated for that frame and the dense velocity fields generated for all intermediate frames between that frame and the final frame.

8. The method of claim 6, wherein an encoder part of the convolutional encoder-decoder comprises a variational autoencoder that forces the estimated deformation field into a latent space distribution that is learned from the training medical image sequences.

9. The method of claim 6, wherein the deep neural network further comprises a memory module that is trained to learn a temporal motion model from the training medical image sequences, and the memory module is implemented using a recurrent neural network or a memory network.

10. The method of claim 6, wherein generating an encoding of observed motion in the medical image sequence using the trained deep neural network comprises:
outputting encoded motion parameters generated by an encoder part of the convolutional encoder-decoder for the frames of the medical image sequence input to the trained deep neural network.

11. The method of claim 10, further comprising:
classifying the medical image sequence based on the encoded motion parameters to detect disease, classify the patient, or predict outcome of a treatment.

12. The method of claim 10, further comprising:
performing motion synthesis from an input medical image that is not in the sequence of medical images using the encoded motion parameters to generate a synthetic sequence of medical images.

13. An apparatus for motion estimation and modeling in a medical image sequence of a patient, comprising:
means for receiving a medical image sequence of a patient;
means for inputting a plurality of frames of the medical image sequence to a trained deep neural network;
means for generating, using the trained deep neural network, diffeomorphic deformation fields representing estimated motion between the frames of the medical image sequence input to the trained deep neural network, wherein the means for generating, using the trained deep neural network, diffeomorphic deformation fields representing estimated motion between the frames of the medical image sequence input to the trained deep neural network comprises:
means for generating, by the trained deep neural network for each frame input to the trained deep neural network, a dense velocity field that provides estimated velocities at each pixel in that frame; and
means for generating a respective diffeomorphic deformation field for each frame input to the trained deep neural network by performing exponentiation of the dense velocity field generated for that frame, wherein the diffeomorphic deformation field provides estimated displacements between that frame and the next frame at each pixel;
means for generating an encoding of observed motion in the medical image sequence using the trained deep neural network; and
means for predicting non-observed motion from the medical image sequence and generating at least one predicted frame using the trained deep neural network, wherein the at least one predicted frame is one of a predicted future frame or a predicted frame between the frames of the medical image sequence input to the trained deep neural network.

14. The apparatus of claim 13, wherein the means for predicting non-observed motion from the medical image sequence and generating at least one predicted frame using the trained deep neural network comprises:
means for generating the at least one predicted frame from a frame input to the trained deep neural network by warping the input frame based on the diffeomorphic deformation field estimated for the input frame.

15. The apparatus of claim 13, wherein the trained deep neural network comprises:
a convolutional encoder-decoder that inputs each frame and includes an output layer that generates a dense velocity field for each frame that provides estimated velocities at each pixel in that frame;

an exponentiation layer that performs exponentiation of the dense velocity field generated for each frame to generate the diffeomorphic deformation field for each frame; and a warping layer that warps each frame based on the diffeomorphic deformation field generated for each frame to generate a predicted next frame for each frame.

16. The apparatus of claim 15, wherein the trained deep neural network is trained based on a plurality of training medical image sequences to minimize a loss function that compares a final frame of each training medical image sequence with a predicted final frame generated from each previous frame in the training medical image sequence by warping each previous frame based on a sum of the dense velocity field generated for that frame and the dense velocity fields generated for all intermediate frames between that frame and the final frame.

17. A non-transitory computer readable medium storing computer program instructions for computer-based motion estimation and modeling in a medical image sequence of a patient, the computer program instructions when executed by a processor cause the processor to perform operations comprising:

receiving a medical image sequence of a patient;
inputting a plurality of frames of the medical image sequence to a trained deep neural network;
generating, using the trained deep neural network, diffeomorphic deformation fields representing estimated motion between the frames of the medical image sequence input to the trained deep neural network, wherein generating, using the trained deep neural network, diffeomorphic deformation fields representing estimated motion between the frames of the medical image sequence input to the trained deep neural network comprises:
generating, by the trained deep neural network for each frame input to the trained deep neural network, a dense velocity field that provides estimated velocities at each pixel in that frame; and
generating a respective diffeomorphic deformation field for each frame input to the trained deep neural network by performing exponentiation of the dense velocity field generated for that frame, wherein the diffeomorphic deformation field provides estimated displacements between that frame and the next frame at each pixel;
generating an encoding of observed motion in the medical image sequence using the trained deep neural network; and
predicting non-observed motion from the medical image sequence and generating at least one predicted frame using the trained deep neural network, wherein the at least one predicted frame is one of a predicted future frame or a predicted frame between the frames of the medical image sequence input to the trained deep neural network.

18. The non-transitory computer readable medium of claim 17, wherein predicting non-observed motion from the medical image sequence and generating at least one predicted frame using the trained deep neural network comprises:

generating a predicted frame between the frames of the medical image sequence by:
inputting a frame of the medical image sequence to the trained deep neural network;
generating, by the trained deep neural network, a predicted dense velocity field that provides estimated velocities at each pixel in the input frame of the medical image sequence;
generating a predicted diffeomorphic deformation field that provides predicted displacements between the input frame and a time point between the input frame and a next frame in the medical image sequence at each pixel by performing exponentiation of the predicted dense velocity field; and
generating a predicted frame between the input frame and the next frame of the medical image sequence by warping the input frame based on the predicted diffeomorphic deformation field.

19. The non-transitory computer readable medium of claim 17, wherein predicting non-observed motion from the medical image sequence and generating at least one predicted frame using the trained deep neural network comprises:

generating a predicted future frame by:
inputting a final frame of the medical image sequence to the trained deep neural network;
generating, by the trained deep neural network, a predicted dense velocity field that provides estimated velocities at each pixel in the final frame of the medical image sequence;
generating a predicted diffeomorphic deformation field by performing exponentiation of the predicted dense velocity field; and
generating a predicted next frame subsequent to the final frame of the medical image sequence by warping the final frame of the medical image sequence based on the predicted diffeomorphic deformation field.

20. The non-transitory computer readable medium of claim 19, wherein predicting non-observed motion from the medical image sequence and generating at least one predicted frame using the trained deep neural network further comprises:

generating a predicted future frame by:
(a) inputting the predicted next frame to the trained deep neural network,
(b) generating, by the trained deep neural network, a predicted dense velocity field for the input predicted next frame,
(c) generating a predicted diffeomorphic deformation field for the input predicted next frame by performing exponentiation of the predicted dense velocity field for the input predicted next frame,
(d) generating a subsequent predicted next frame by warping the input predicted next frame based on the predicted diffeomorphic deformation field generated for the input predicted next frame, and
(e) repeating operations (a)-(d) for each of plurality of predicted next frames.

21. The non-transitory computer readable medium of claim 17, wherein the trained deep neural network comprises:

a convolutional encoder-decoder that inputs each frame and includes an output layer that generates a dense velocity field for each frame that provides estimated velocities at each pixel in that frame;

an exponentiation layer that performs exponentiation of the dense velocity field generated for each frame to generate the diffeomorphic deformation field for each frame; and a warping layer that warps each frame based on the diffeomorphic deformation field generated for each frame to generate a predicted next frame for each frame.

22. The non-transitory computer readable medium of claim 21, wherein the trained deep neural network is trained based on a plurality of training medical image sequences to minimize a loss function that compares a final frame of each training medical image sequence with a predicted final frame generated from each previous frame in the training medical image sequence by warping each previous frame based on a sum of the dense velocity field generated for that frame and the dense velocity fields generated for all intermediate frames between that frame and the final frame.

* * * * *